United States Patent
Rowlandson et al.

(10) Patent No.: US 8,808,185 B2
(45) Date of Patent: Aug. 19, 2014

(54) SYSTEM AND METHOD FOR GENERATING A PATIENT DIAGNOSIS

(75) Inventors: Gordon Ian Rowlandson, Milwaukee, WI (US); Kjell Kristoffersen, Oslo (NO); Alfred Lojewski, Brookfield, WI (US); Brian Young, Germantown, WI (US)

(73) Assignee: General Electric Company, Schenectady, NY (US)

( * ) Notice: Subject to any disclaimer, the term of this patent is extended or adjusted under 35 U.S.C. 154(b) by 859 days.

(21) Appl. No.: 12/057,578

(22) Filed: Mar. 28, 2008

(65) Prior Publication Data
US 2009/0247872 A1    Oct. 1, 2009

(51) Int. Cl.
A61B 5/0402 (2006.01)
A61B 8/13 (2006.01)
A61B 8/06 (2006.01)
A61B 8/08 (2006.01)
G06F 19/00 (2011.01)

(52) U.S. Cl.
CPC .......... *A61B 5/0402* (2013.01); *A61B 8/06* (2013.01); *A61B 8/0858* (2013.01); *A61B 8/0883* (2013.01); *G06F 19/345* (2013.01)
USPC ........... 600/438; 600/437; 600/443; 600/463; 600/509; 600/513; 705/2

(58) Field of Classification Search
CPC ...... A61B 5/0402; A61B 8/06; A61B 8/0858; A61B 8/0883; G06F 19/345
USPC ............... 600/16, 17, 18, 437, 438, 443, 463, 600/509; 705/2
See application file for complete search history.

(56) References Cited

U.S. PATENT DOCUMENTS

| | | | |
|---|---|---|---|
| 6,334,849 B1 | 1/2002 | Sunagawa | |
| 6,370,423 B1 | 4/2002 | Guerrero et al. | |
| 6,569,101 B2 | 5/2003 | Quistgaard et al. | |
| 6,665,559 B2 * | 12/2003 | Rowlandson | 600/515 |
| 6,953,436 B2 | 10/2005 | Watrous et al. | |
| 6,962,566 B2 | 11/2005 | Quistgaard et al. | |
| 7,074,187 B2 | 7/2006 | Selzer et al. | |
| 7,200,439 B2 * | 4/2007 | Zdeblick et al. | 607/17 |
| 7,494,459 B2 * | 2/2009 | Anstadt et al. | 600/17 |
| 7,686,766 B2 | 3/2010 | Quistgaard et al. | |

(Continued)

FOREIGN PATENT DOCUMENTS

| | | |
|---|---|---|
| CN | 101147687 A | 3/2008 |
| JP | 2003-93388 A | 4/2003 |
| WO | 2005/037096 A1 | 4/2005 |

OTHER PUBLICATIONS

English translation of Chinese Office Action issued in CN Application No. 200910133867.3.

(Continued)

*Primary Examiner* — Baisakhi Roy
(74) *Attorney, Agent, or Firm* — Andrus Intellectual Property Law, LLP

(57) ABSTRACT

A system for generating a diagnosis is disclosed herein. The system includes a controller, an electrocardiograph connected to the controller, and an ultrasound device connected to the controller. The electrocardiograph is configured to generate a diagnostic electrocardiogram. The controller is configured to generate a diagnosis based on data from the electrocardiograph or the ultrasound device.

22 Claims, 2 Drawing Sheets

(56) References Cited

U.S. PATENT DOCUMENTS

| | | | |
|---|---|---|---|
| 8,137,273 B2 | 3/2012 | Everett et al. | |
| 2006/0206033 A1* | 9/2006 | Guerrero et al. | 600/523 |
| 2007/0112593 A1* | 5/2007 | Daya | 705/2 |
| 2008/0077012 A1* | 3/2008 | Gunji | 600/443 |
| 2008/0213214 A1* | 9/2008 | Terzic et al. | 424/85.2 |
| 2008/0312536 A1* | 12/2008 | Dala-Krishna | 600/459 |
| 2010/0168578 A1* | 7/2010 | Garson et al. | 600/443 |

OTHER PUBLICATIONS

Unofficial translation of JPO Office Action Rejection for JP Application No. 2009-072995 dated Aug. 20, 2013.

http://www.uvapf.org/technologies/index.cfm/fuseaction/invention/invention_id/392/?CFID=841160&CFTOKEN=80454629&, Mar. 26, 2008.

English translation of Japanese Final Rejection for JP Application No. 2009-072995 dated May 27, 2014.

English translation of "Guidelines for Diagnosing and Treatment of Patients with Hypertrophic Cardiomyopathy", JCS, Nov. 25, 2007, http://www.j-circ.or.jp/guideline/pdf/JCS2007_doi_h.pdf, pp. 10-15.

* cited by examiner

SYSTEM AND METHOD FOR GENERATING A PATIENT DIAGNOSIS

BACKGROUND OF THE INVENTION

The subject matter disclosed herein relates to a system and method for generating a patient diagnosis. More specifically, the subject matter disclosed herein relates to a system for generating a patient diagnosis based on input from an electrocardiograph and/or an ultrasound device, and a method for implementing the system.

Left ventricular hypertrophy (LVH) refers to an increased heart chamber size or a thickening of the myocardium of the left ventricle of the heart. LVH is not itself a disease but is indicative of hypertrophic cardiomyopathy (HCM); which refers to a disease affecting the muscle of the heart. Accordingly, LVH may be identified as a means for diagnosing an otherwise undetectable HCM.

LVH is generally identified using electrocardiography or echocardiography. A problem with diagnosing HCM based on an electrocardiographic LVH analysis is that electrocardiography can only indirectly estimate myocardium thickness based on cardiac electrical activity, and is therefore potentially imprecise. A problem with diagnosing HCM based on an echocardiographic LVH measurement is that the echocardiographic measurement is labor intensive, expensive and time consuming. Another problem with diagnosing HCM based on an echocardiographic LVH measurement is that the echocardiographic measurement may identify an enlarged myocardium that is otherwise healthy and could thereby yield an inappropriate HCM diagnosis. As an example, an athletic patient with an enlarged myocardium that is attributable to aerobic exercise could be inappropriately diagnosed with HCM based on an echocardiographic LVH measurement.

BRIEF DESCRIPTION OF THE INVENTION

The above-mentioned shortcomings, disadvantages and problems are addressed herein which will be understood by reading and understanding the following specification.

In an embodiment, a system includes a controller, an electrocardiograph connected to the controller, and an ultrasound device connected to the controller. The electrocardiograph is configured to generate a diagnostic electrocardiogram. The controller is configured to generate a diagnosis based on data from the electrocardiograph or the ultrasound device.

In another embodiment, a system includes a controller; and an electrocardiograph connected to the controller. The electrocardiograph is configured to generate a diagnostic electrocardiogram, and to provide voltage criteria data and ECG pathology data based on the diagnostic electrocardiogram. The system also includes an ultrasound device connected to the controller. The ultrasound device is configured to provide a myocardium structural measurement. The controller is configured to generate a diagnosis based on the voltage criteria data, the ECG pathology data and the myocardium structural measurement.

In another embodiment, a method includes providing a system comprising an electrocardiograph and an ultrasound device, and implementing the system to obtain a diagnostic electrocardiogram. The method also includes implementing the system to analyze a voltage criteria and an ECG pathology of the diagnostic electrocardiogram. The method also includes implementing the system to obtain an ultrasonic image of the patient, and implementing the ultrasonic image to obtain a myocardium structural measurement. The method also includes generating a diagnosis based on the voltage criteria analysis, the ECG pathology, and the myocardium structural measurement.

In another embodiment, a method includes providing a system comprising an electrocardiograph and an ultrasound device, and implementing the electrocardiograph to obtain a diagnostic electrocardiogram. The method also includes generating an integrated report comprising ECG data from the diagnostic electrocardiogram, and ultrasound data from the ultrasound device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
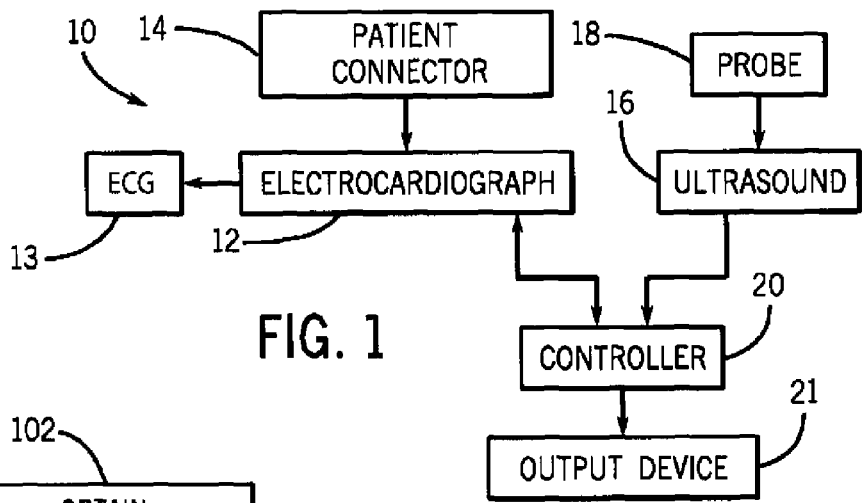
FIG. 1 is a schematic representation of a system in accordance with an embodiment.

Referring to FIG. 1, a system 10 is shown in accordance with one embodiment. The system 10 includes an electrocardiograph 12, a patient connector 14, an ultrasound device 16, an ultrasound probe 18, and a controller 20.

The electrocardiograph 12 is connected to the patient connector 14. The patient connector 14 generally include array of sensors or transducers adapted for direct attachment to a patient. According to one embodiment, the patient connector 14 comprise four sensors adapted for attachment to a patient's limbs, and six additional sensors adapted for attachment to the patient's torso. In other embodiments, alternative configurations of sensors and sensor locations can be used to acquire a standard or non-standard electrocardiogram (ECG) signal. For example, the sensors may be placed in modified locations such as the Mason-Likar lead configuration, or fewer sensors may be used to obtain a derived diagnostic 12 lead electrocardiogram.

The electrocardiograph 12 is adapted to record a patient's cardiac electrical activity. The electrocardiograph 12 can generate an ECG 13 comprising a plot of the recorded cardiac electrical over time. The electrocardiograph 12 may also be implemented to diagnose left ventricular hypertrophy (LVH) based on one or more criteria pertaining the recorded cardiac electrical activity. For example, LVH can be diagnosed based on voltage criteria such as the Sokolow and Lyon criteria, and/or the Cornell criteria. Voltage criteria are well known to those skilled in the art and therefore will not be described in detail.

The ultrasound device 16 is connected to the ultrasound probe 18. In a non-limiting manner, the ultrasound device 16 may be operational in one or more of the following modes: 2-D imaging or B-mode, M-mode, color flow mapping, color M-mode, tissue velocity imaging, and power Doppler. These modes are well known to those skilled in the art and therefore will not be described in detail. 3-D imaging may also be used. The ultrasound device 16 is adapted to obtain ultrasound data that may, for example, include one or more of the following data types: dimensions, time differences between cardiac events, velocity of tissue or blood, and tissue compression. Additionally, for purposes of this disclosure, the term ultrasound data should be defined to include other data types that are derivable from the aforementioned exemplary data types.

The ultrasound probe 18 is adapted to facilitate convenient and precise imaging of targeted cardiac regions. The ultrasound device 16 can be implemented to diagnose LVH by imaging the myocardium of the left ventricle, and thereafter implementing the imaging data to obtain myocardium structural measurements such as myocardium wall thickness, myocardium mass or left ventricular inner diameter. As an example, LVH may be diagnosed if the measured myocardium wall thickness exceeds 1.1 centimeters.

The controller 20 is connected to the electrocardiograph 12 and the ultrasound device 16. The controller 20 can also be connected to an output device 21. The output device may comprise any known device adapted to transmit or convey data from the controller such as, for example, a monitor, a printer, or a device adapted to transmit digital records from the controller 20. As will be described in detail hereinafter, the controller 20 can be configured to generate a diagnosis based on data or input from the electrocardiograph 12 and/or the ultrasound device 16. According to one embodiment, the diagnosis from the controller may comprise an integrated report that contains both ECG and ultrasonic data, and an interpretation of the LVH diagnosis including an assessment of the pathologic severity of LVH. The diagnosis from the controller 20 may be conveyed via the ECG 13 and/or the output device 21.

Figure 2:
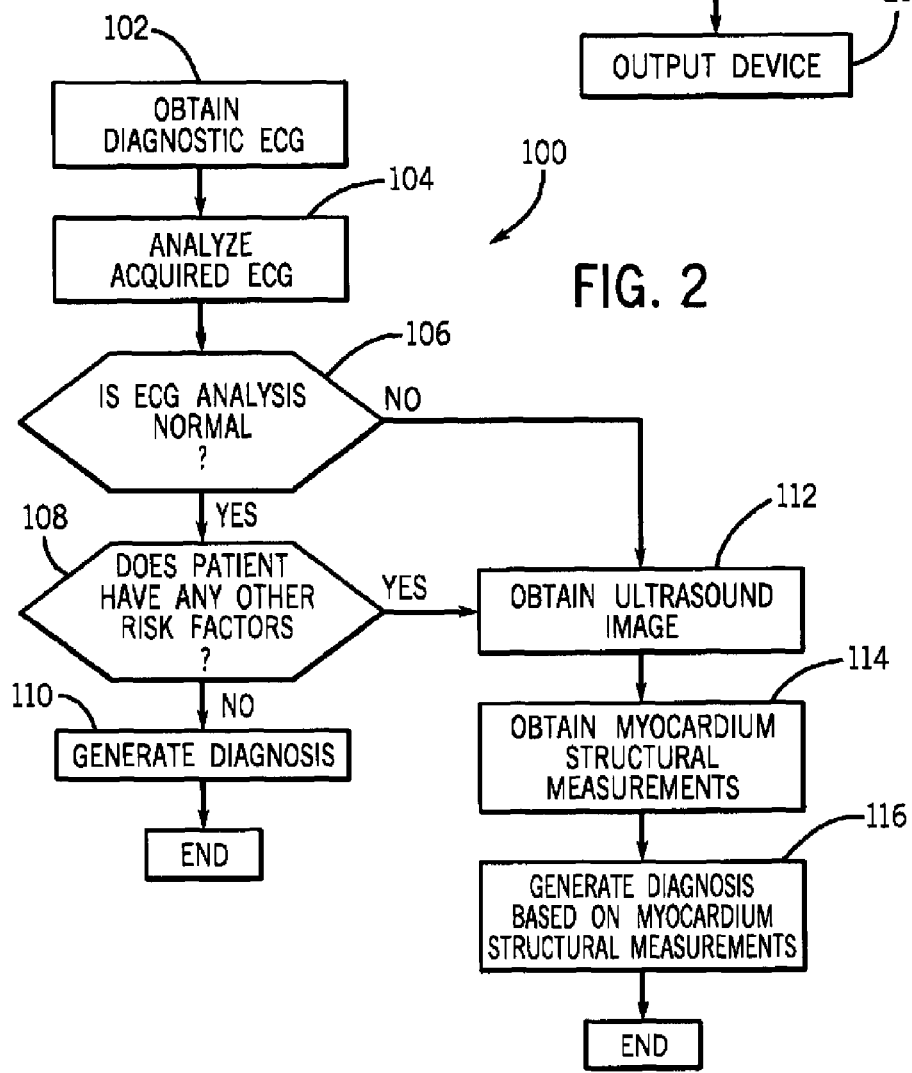
FIG. 2 is flow chart illustrating a method in accordance with an embodiment.

Referring to FIG. 2, a flow chart illustrating a method 100 for implementing the system 10 (shown in FIG. 1) in order to diagnose LVH is shown in accordance with an embodiment. The method 100 includes blocks 102-116 which represent a series of steps. Steps 102-116 need not necessarily be performed in the order shown.

Referring to FIGS. 1 and 2, at step 102 a diagnostic ECG is obtained using the electrocardiograph 12. For purposes of this disclosure, a diagnostic ECG should be defined as comprising a standardized 12 lead representation of cardiac electrical activity, or a Frank lead representation of cardiac electrical activity. A diagnostic ECG should also be defined as being acquired at a minimum sampling rate of 500 samples per second, at a minimum bandwidth of 0.5-150 Hz, and at a minimum sample resolution of 5 microvolts.

At step 104, the diagnostic ECG obtained at step 102 is analyzed by the electrocardiograph 12. Step 104 generally includes an analysis of voltage criteria such as the Sokolow and Lyon criteria, and/or the Cornell criteria. Step 104 may also include an analysis involving other criteria that are symptomatic of LVH such as the presence of atrial fibrillation, P-wave duration, P-wave morphology, etc. It has been observed that a wide variety of ECG abnormalities are correlated with LVH such that, according to one embodiment, any detectable ECG abnormality may be considered in the analysis of step 104.

At step 106, the method 100 determines if the diagnostic ECG is normal based on the analysis of step 104. It should be appreciated that this determination is predicated on the specific criteria implemented at step 104. For illustrative purposes a "normal ECG" will hereinafter be described as an ECG without any detectable abnormalities; however, alternate embodiments may define a normal ECG based on different criteria. If at step 106 the diagnostic ECG is determined to be normal, the method 100 proceeds to step 108. If at step 106 the diagnostic ECG is determined to be abnormal, the method 100 proceeds to step 112.

At step 108, the method 100 determines whether a given patient has any additional risk factors associated with LVH such as, for example, high blood pressure (HBP), pre-HBP, diabetes, mitral valve insufficiencies, or aortic stenosis. If at step 108 it is determined that there are no additional risk factors, the method 100 proceeds to step 110. If at step 108 it is determined that there are additional risk factors, the method 100 proceeds to step 112.

At step 110, the method 100 generates a negative diagnosis for LVH. According to one embodiment, this diagnosis may be automatically generated by the controller 20 and conveyed along with the other data included in the patient's diagnostic ECG.

At step 112, the ultrasound device 16 is implemented to acquire an ultrasonic image of the patient's myocardium. At step 114, the acquired ultrasonic image is implemented to obtain one or more myocardium structural measurements. At step 116, the method 100 generates a diagnosis based on the myocardium structural measurements. According to one embodiment, the controller 20 automatically generates a positive LVH diagnosis if myocardium wall thickness exceeds 1.1 centimeters, and a negative LVH diagnosis if myocardium wall thickness is less than or equal to 1.1 centimeters. The diagnosis generated at step 116 may be conveyed along with the other data included in the patient's diagnostic ECG.

It should be appreciated that the method 100 exclusively implements the electrocardiograph 12 to evaluate a patient unless a risk factor associated with LVH is identified. Accordingly, when evaluating low risk patients, the method 100 saves labor, expense and time associated with an ultrasonic evaluation. If an LVH risk factor is identified, the method 100 implements the ultrasound device 16 to providing a more accurate LVH diagnosis than would otherwise be obtainable from an electrocardiograph.

Figure 3:
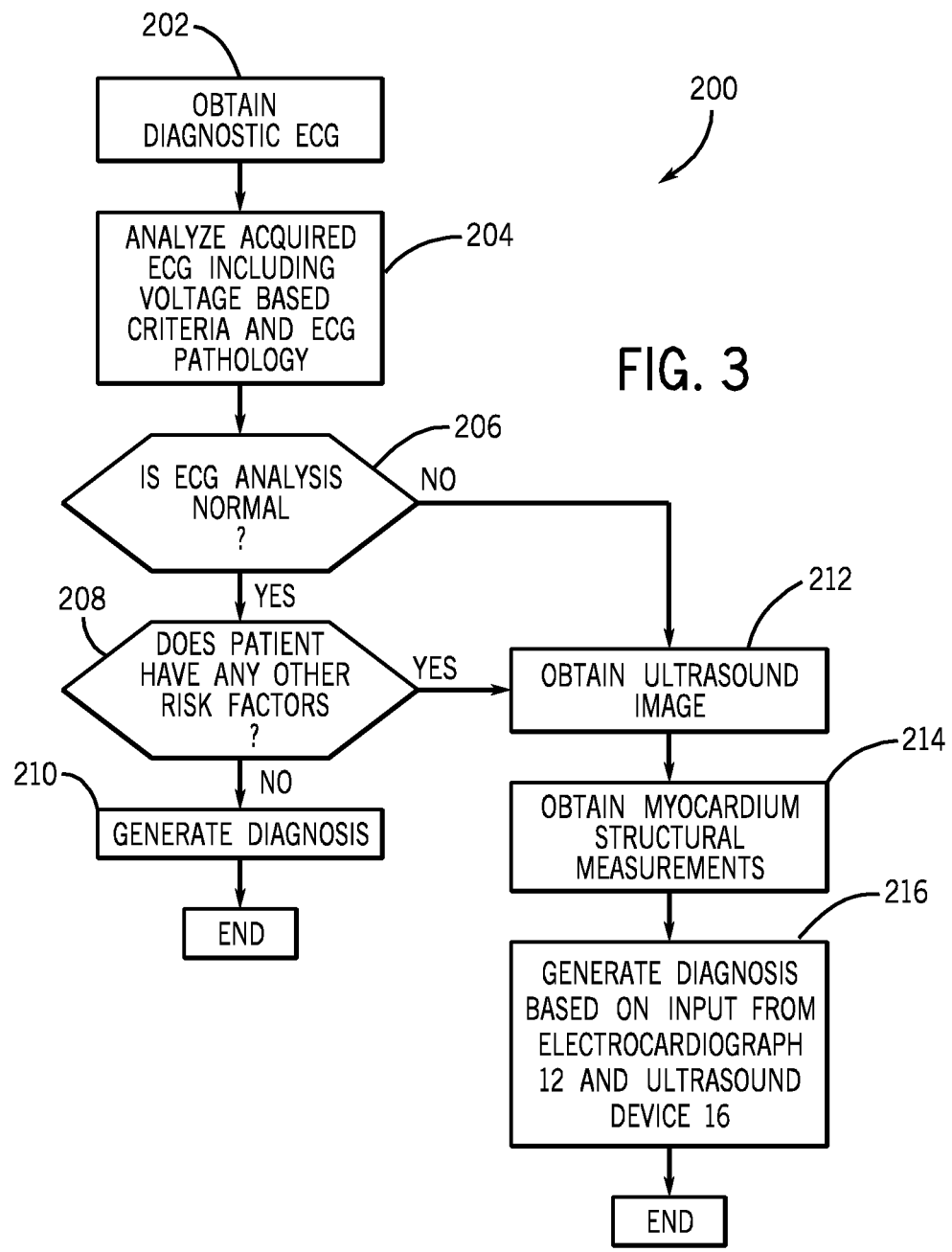
FIG. 3 is flow chart illustrating a method in accordance with another embodiment.

Referring to FIG. 3, a flow chart illustrates an embodiment of a method 200 for implementing the system 10 (shown in FIG. 1) to diagnose LVH and hypertrophic cardiomyopathy (HCM). The method 200 may also provide a severity rating adapted to convey the seriousness of the diagnosed condition. It should be appreciated that the integration of both ECG and ultrasonic data embodied in method 200 enables the generation of an assessment of the pathologic nature of LVH conditions, which may necessitate medical intervention. The method 200 includes blocks 202-216 which represent a series of steps. Steps 202-216 need not necessarily be performed in the order shown.

Referring to FIGS. 1 and 3, at step 202 a diagnostic ECG is obtained using the electrocardiograph 12. At step 204, the diagnostic ECG is analyzed by the electrocardiograph 12. Step 204 will hereinafter be described as analyzing the diagnostic ECG for purposes of identifying any detectable ECG abnormalities; however, alternate embodiments may analyze the diagnostic ECG based on other criteria. The diagnostic ECG analysis of step 104 specifically includes an analysis of voltage criteria such as the Sokolow and Lyon criteria, and/or the Cornell criteria, and further includes an analysis of ECG pathology data. In a non-limiting manner, the ECG pathology data may include QRS duration, and data pertaining to repolarization abnormalities.

At step 206, the method 200 determines if the diagnostic ECG is normal based on the analysis of step 204. It should be appreciated that this determination is predicated on the specific criteria implemented at step 204. For illustrative purposes a "normal ECG" will hereinafter be described as an ECG without any detectable abnormalities; however, alternate embodiments may define a normal ECG based on different criteria. If at step 206 the diagnostic ECG is determined to be normal, the method 200 proceeds to step 208. If at step 206 the diagnostic ECG is determined to be abnormal, the method 200 proceeds to step 212.

At step 208, the method 200 determines whether a given patient has any additional risk factors associated with LVH such as, for example, HBP, pre-HBP, diabetes, mitral valve insufficiencies, or aortic stenosis. If at step 208 it is determined that there are no additional risk factors, the method 200 proceeds to step 210. If at step 208 it is determined that there are additional risk factors, the method 200 proceeds to step 212.

At step 210, the method 200 generates a negative diagnosis for LVH. According to one embodiment, this diagnosis may be automatically generated by the controller 20 and conveyed along with the other data included in the patient's diagnostic ECG.

At step 212, the ultrasound device 16 is implemented to acquire an ultrasonic image of the patient's myocardium. At step 214, the acquired ultrasonic image is implemented to obtain one or more myocardium structural measurements. At step 216, the method 100 generates a diagnosis based on input from the electrocardiograph 12 and the ultrasound 16. As step 216 implements both the electrocardiograph 12 and the ultrasound 16, the resultant diagnosis is potentially more accurate and complete than that which would be available based on input from either device individually. According to one embodiment, the diagnosis of step 216 is automatically generated by the controller 20 based on voltage criteria and ECG pathology data from the electrocardiograph 12, and on myocardium structural measurement data from the ultrasound device 16. According to another embodiment, the diagnosis of step 216 includes a patient severity rating.

The following section will provide several non-limiting examples in which step 216 of the method 200 can implement data from both the electrocardiograph 12 and the ultrasound device 16 to generate a diagnosis.

Assume for purposes of a first exemplary embodiment that an electrocardiographic evaluation of given patient is negative based on a voltage criteria analysis and positive based on an ECG pathology analysis, and further that an ultrasonic evaluation of the same patient indicates a myocardium wall thickness greater than 1.1 centimeters. In this example, the excessive myocardium wall thickness in combination with the abnormal ECG pathology finding provide a strong indication of LVH and HCM. The negative ECG voltage criteria analysis is not sufficient to change the overall diagnosis but may reduce the associated severity rating. Accordingly, step 216 of the method 200 may generate a diagnosis that is positive for LVH based on larger than normal myocardium wall thickness, and positive for HCM. The diagnosis may also include a medium severity rating.

Assume for purposes of a second exemplary embodiment that an electrocardiographic evaluation of given patient is negative based on a voltage criteria analysis and negative based on an ECG pathology analysis, and further that an ultrasonic evaluation of the same patient indicates a myocardium wall thickness greater than 1.1 centimeters. In this example, the excessive myocardium wall thickness is mitigated by the voltage criteria and pathology findings. More precisely, a large myocardium wall thickness in the absence of an ECG pathology abnormality may indicate that the wall thickness is unrelated to HCM. Accordingly, step 216 of the method 200 may generate a diagnosis that is negative for HCM and that includes a low severity rating. The diagnosis may also indicate that a larger than normal myocardium wall thickness has been identified but that it is likely a normal variant or attributable to aerobic activity.

Assume for purposes of a third exemplary embodiment that an electrocardiographic evaluation of given patient is positive based on a voltage criteria analysis and negative based on an ECG pathology analysis, and further that an ultrasonic evaluation of the same patient indicates a myocardium wall thickness less than 1.1 centimeters. In this example, the normal myocardium wall thickness and normal ECG pathology indicate the absence of LVH and HCM. The positive ECG voltage criteria analysis would likely be considered a normal variant or a misdiagnosis in light of the more conclusive wall thickness measurement and pathology analysis; however, the voltage criteria finding may still be conveyed as a precautionary measure. Accordingly, step 216 of the method 200 may generate a diagnosis identifying a positive ECG voltage criteria finding that is likely to be a normal variant. The diagnosis may also include a low severity rating.

Assume for purposes of a fourth exemplary embodiment that an electrocardiographic evaluation of given patient is negative based on a voltage criteria analysis and positive based on an ECG pathology analysis, and further that an ultrasonic evaluation of the same patient indicates a myocardium wall thickness less than 1.1 centimeters. In this example, the normal myocardium wall thickness and normal voltage criteria analysis indicate the absence of LVH. The positive ECG pathology analysis may, however, indicate the presence of a potentially acute disease unrelated to LVH. Accordingly, step 216 of the method 200 may generate a diagnosis that is negative for LVH. The diagnosis may also identify the positive ECG finding with a medium to high severity rating.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A system comprising:
a controller;
a diagnostic electrocardiograph connected to the controller, said diagnostic electrocardiograph being configured to obtain a diagnostic electrocardiogram from a patient; and
an ultrasound device connected to the controller, wherein the controller implements the ultrasound device to obtain an ultrasound image from the patient in response to the diagnostic electrocardiogram having an abnormal analysis or the patient having a risk factor,
wherein said controller is configured to generate a diagnosis based on data from the electrocardiograph and the ultrasound device when the ultrasound image is obtained, and is further configured to generate the diagnosis based on data from the electrocardiograph only in response to the diagnostic electrocardiogram having a normal analysis and the patient having no risk factors.

2. The system of claim 1, wherein said controller is configured to generate a diagnosis based on data from the diagnostic electrocardiograph and the ultrasound device.

3. The system of claim 2, wherein said controller is configured to generate a diagnosis based on voltage criteria data and ECG pathology analysis data from the diagnostic electrocardiograph, and on myocardium structural measurement data from the ultrasound device.

4. The system of claim 1, wherein said controller is configured to generate a diagnosis based exclusively on myocardium structural measurement data from the ultrasound device if a risk factor associated with left ventricular hypertrophy is identified.

5. The system of claim 1, wherein said controller is configured to diagnose left ventricular hypertrophy and/or hypertrophic cardiomyopathy.

6. The system of claim 1, wherein said controller is configured to generate a severity rating based on data from the diagnostic electrocardiograph or the ultrasound device.

7. The system of claim 1, wherein said controller is configured to convey the diagnosis via the diagnostic electrocardiogram.

8. The system of claim 1, wherein said controller is configured to generate an integrated report comprising input from the diagnostic electrocardiograph and the ultrasound device.

9. A system comprising:
a controller;
a diagnostic electrocardiograph connected to the controller, said diagnostic electrocardiograph being configured to obtain a diagnostic electrocardiogram from a patient, said diagnostic electrocardiograph also being configured to provide voltage criteria data and ECG pathology data based on the diagnostic electrocardiogram; and
an ultrasound device connected to the controller, said ultrasound device being configured to obtain a myocardium structural measurement from the patient, wherein the controller implements the ultrasound device to obtain an ultrasound image from the patient in response to the diagnostic electrocardiogram having an abnormal analysis or the patient having a risk factor,
wherein said controller is configured to generate a diagnosis based on the voltage criteria data, the ECG pathology data and the myocardium structural measurement when the ultrasound image is obtained, and is further configured to generate the diagnosis based on data from the electrocardiograph only in response to the diagnostic electrocardiogram having a normal analysis and the patient having no risk factors.

10. The system of claim 9, wherein said controller is configured to diagnose left ventricular hypertrophy and/or hypertrophic cardiomyopathy.

11. The system of claim 9, wherein said controller is configured to generate a severity rating based on data from the diagnostic electrocardiograph or the ultrasound device.

12. The system of claim 9, wherein said controller is configured to convey the diagnosis via an output device selected from the group consisting of a monitor, a printer, and a data transmission device.

13. The system of claim 9, wherein said controller is configured to generate an integrated report comprising input from the diagnostic electrocardiograph and the ultrasound device.

14. The system of claim 13, wherein the integrated report comprises a left ventricular hypertrophy diagnosis, a hypertrophic cardiomyopathy diagnosis, and/or a severity rating.

15. The system of claim 13, further comprising an output device selected from the group consisting of a monitor, a printer and a data transmission device, said output device being configured to convey the integrated report.

16. A method comprising:
providing a system comprising a diagnostic electrocardiograph and an ultrasound device:
implementing the system to obtain a diagnostic electrocardiogram from a patient;
implementing the system to analyze a voltage criteria and an ECG pathology of the diagnostic electrocardiogram:
implementing the system to obtain an ultrasonic image of the patient in response to the voltage criteria or the ECG pathology having an abnormal analysis, or in response to the patient having a risk factor,
obtaining a myocardium structural measurement from the ultrasonic image; and
generating a diagnosis based on the voltage criteria analysis, the ECG pathology, and the myocardium structural measurement when the ultrasound image is obtained, and is further configured to generate the diagnosis based on data from the electrocardiograph only in response to the diagnostic electrocardiogram having a normal analysis and the patient having no risk factors.

17. The method of claim 16, wherein said generating a diagnosis includes generating a left ventricular hypertrophy diagnosis.

18. The method of claim 16, wherein said generating a diagnosis includes generating a hypertrophic cardiomyopathy diagnosis.

19. The method of claim 16, further comprising generating a severity rating based on one of the voltage criteria, the ECG pathology, and the myocardium structural measurement.

20. A method comprising:
providing a system comprising a diagnostic electrocardiograph and an ultrasound device;
implementing the diagnostic electrocardiograph to obtain a diagnostic electrocardiogram from a patient and thriller obtaining an ultrasonic image from the patient in response to the voltage criteria or the ECG pathology having an abnormal analysis, or in response to the patient having a risk factor, and
generating, an integrated report comprising ECG data from the diagnostic electrocardiogram, and ultrasound data from the ultrasound image when the ultrasound image is obtained, and is further configured to generate the diagnosis based on data from the electrocardiograph only is response to the diagnostic electrocardiogram having a normal analysis and the patient having no risk factors.

21. The method of claim 20, wherein said generating an integrated report includes generating an integrated report comprising a left ventricular hypertrophy diagnosis, a hypertrophic cardiomyopathy diagnosis and/or a severity rating.

22. The method of claim 21, further comprising conveying the integrated report via an output device selected from the group consisting of a monitor, a printer and a data transmission device.

* * * * *